US009791466B2

(12) United States Patent
Neeper

(10) Patent No.: US 9,791,466 B2
(45) Date of Patent: Oct. 17, 2017

(54) METHOD AND DEVICE FOR COMPENSATION FOR DIMENSIONAL VARIATIONS IN LOW TEMPERATURE SAMPLE GROUP HOLDERS

(75) Inventor: Robert K. Neeper, Ramona, CA (US)

(73) Assignee: Brooks Automation, Inc., Chelmsford, MA (US)

( * ) Notice: Subject to any disclaimer, the term of this patent is extended or adjusted under 35 U.S.C. 154(b) by 1019 days.

(21) Appl. No.: 13/555,957

(22) Filed: Jul. 23, 2012

(65) Prior Publication Data

US 2013/0028697 A1  Jan. 31, 2013

Related U.S. Application Data

(60) Provisional application No. 61/510,455, filed on Jul. 21, 2011.

(51) Int. Cl.
| | | |
|---|---|---|
| *B25J 9/00* | (2006.01) | |
| *B65G 1/06* | (2006.01) | |
| *G01N 35/00* | (2006.01) | |
| *G01N 35/04* | (2006.01) | |

(52) U.S. Cl.
CPC ......... *G01N 35/0099* (2013.01); *G01N 35/04* (2013.01); *G01N 2035/00435* (2013.01)

(58) Field of Classification Search
None
See application file for complete search history.

(56) References Cited

U.S. PATENT DOCUMENTS

| | | | |
|---|---|---|---|
| 3,377,838 A | | 4/1968 | Kanazawa et al. |
| 4,298,285 A | | 11/1981 | Ito |
| 4,300,836 A | | 11/1981 | Holmes et al. |
| 4,335,962 A | | 6/1982 | Di Matteo et al. |
| 4,409,530 A | * | 10/1983 | Neeper et al. ................ 318/685 |
| 4,564,294 A | | 1/1986 | Ernst |
| 4,593,967 A | | 6/1986 | Haugen |
| 4,641,972 A | | 2/1987 | Halioua et al. |
| 4,653,104 A | | 3/1987 | Tamura |
| 4,654,872 A | | 3/1987 | Hisano et al. |
| 4,705,016 A | * | 11/1987 | Sekiya ........................ 125/13.01 |

(Continued)

FOREIGN PATENT DOCUMENTS

| | | |
|---|---|---|
| EP | 0628823 A1 * | 9/1994 |
| EP | 0 628 823 A1 | 12/1994 |

(Continued)

*Primary Examiner* — Jill Warden
*Assistant Examiner* — Benjamin R Whatley
(74) *Attorney, Agent, or Firm* — Perman & Green, LLP; Colin C. Durham

(57) ABSTRACT

An apparatus includes a pick head configured to transfer sample containers to and from a sample group holder, at least one sensor connected to the pick head and configured to detect at least one predetermined feature of the sample group holder, and a controller configured to receive a detection signal from the at least one sensor corresponding to detection of the at least one predetermined feature, determine a change in a predetermined characteristic of the sample group holder based on a detected position of the at least one predetermined feature, and determine a location of one or more samples in the sample group holder to allow for the transfer of the one or more sample containers to and from the sample group holder based on the edge detection signal.

20 Claims, 9 Drawing Sheets

(56) References Cited

U.S. PATENT DOCUMENTS

| | | |
|---|---|---|
| 4,705,401 A | 11/1987 | Addleman et al. |
| 4,757,210 A | 7/1988 | Bharat et al. |
| 4,796,997 A | 1/1989 | Svetkoff et al. |
| 4,945,631 A | 8/1990 | Banner et al. |
| 5,182,687 A | 1/1993 | Campbell et al. |
| 5,226,782 A | 7/1993 | Rigling |
| 5,237,468 A | 8/1993 | Ellis |
| 5,287,459 A | 2/1994 | Gniewek |
| 5,308,222 A | 5/1994 | Bacchi et al. |
| 5,314,055 A | 5/1994 | Gordon |
| 5,513,948 A | 5/1996 | Bacchi et al. |
| 5,540,889 A | 7/1996 | Gordon et al. |
| 5,589,942 A | 12/1996 | Gordon |
| 5,601,141 A | 2/1997 | Gordon et al. |
| 5,621,529 A | 4/1997 | Gordon et al. |
| 5,645,351 A | 7/1997 | Nakata et al. |
| 5,659,396 A | 8/1997 | Mondie |
| 5,852,672 A | 12/1998 | Lu |
| 6,094,269 A | 7/2000 | Ben-Dove et al. |
| 6,100,984 A | 8/2000 | Chen et al. |
| 6,219,461 B1 | 4/2001 | Wallack |
| 6,256,099 B1 | 7/2001 | Kaufman et al. |
| 6,269,197 B1 | 7/2001 | Wallack |
| 6,443,022 B1 | 9/2002 | Gordon |
| 6,444,996 B1 | 9/2002 | Boenick et al. |
| 6,445,814 B2 | 9/2002 | Iijima et al. |
| 6,483,950 B1 | 11/2002 | Wallack |
| 6,538,244 B1 * | 3/2003 | Skunes ............ 250/208.1 |
| 6,549,288 B1 | 4/2003 | Migdal et al. |
| 6,577,923 B1 * | 6/2003 | White et al. ............ 700/245 |
| 6,610,993 B2 | 8/2003 | Meyhofer et al. |
| 6,809,823 B2 | 10/2004 | Kennedy et al. |
| 6,823,080 B2 | 11/2004 | Iijima et al. |
| 6,868,194 B2 | 3/2005 | Tu et al. |
| 6,983,872 B2 | 1/2006 | Cheng et al. |
| 7,065,242 B2 | 6/2006 | Petrov et al. |
| 7,075,958 B2 | 7/2006 | Wickman et al. |
| 7,103,482 B2 | 9/2006 | Steele et al. |
| 7,190,446 B2 | 3/2007 | Cheng et al. |
| 7,239,399 B2 | 7/2007 | Duquette et al. |
| 7,279,695 B2 | 10/2007 | Oguri |
| 7,337,076 B2 | 2/2008 | Steele et al. |
| 7,364,922 B2 | 4/2008 | Shimizu |
| 7,474,803 B2 | 1/2009 | Petrov et al. |
| 7,485,975 B2 | 2/2009 | Aoyama |
| 7,492,450 B2 | 2/2009 | Harding et al. |
| 7,545,514 B2 | 6/2009 | Manickam et al. |
| 7,555,831 B2 | 7/2009 | Case |
| 7,559,134 B2 | 7/2009 | Gaida |
| 7,620,209 B2 | 11/2009 | Stevick et al. |
| 7,634,365 B2 | 12/2009 | Steele et al. |
| 7,652,754 B2 * | 1/2010 | Barrows ............ 356/28 |
| 7,684,053 B2 | 3/2010 | Chow |
| 7,706,595 B2 | 4/2010 | Bushman et al. |
| 7,751,046 B2 * | 7/2010 | Levy et al. ............ 356/401 |
| 7,777,483 B2 | 8/2010 | Lei et al. |
| 7,813,559 B2 | 10/2010 | Duquette et al. |
| 7,911,600 B2 | 3/2011 | Terasawa et al. |
| 7,916,281 B2 | 3/2011 | Haddock |
| 7,971,542 B2 | 7/2011 | Block et al. |
| 7,978,342 B2 | 7/2011 | Fakhruddin |
| 8,023,110 B1 | 9/2011 | Ngai et al. |
| 8,205,958 B2 | 6/2012 | Endo |
| 2002/0003997 A1 | 1/2002 | Orinski et al. |
| 2003/0026732 A1 | 2/2003 | Gordon et al. |
| 2003/0111494 A1 * | 6/2003 | Lin et al. ............ 222/505 |
| 2005/0137751 A1 * | 6/2005 | Cox et al. ............ 700/245 |
| 2006/0254379 A1 | 11/2006 | Burchyett |
| 2007/0112465 A1 * | 5/2007 | Sadighi et al. ............ 700/254 |
| 2007/0172396 A1 | 7/2007 | Neeper |
| 2007/0231785 A1 * | 10/2007 | Hoyt et al. ............ 435/4 |
| 2008/0044263 A1 * | 2/2008 | Neeper et al. ............ 414/288 |
| 2008/0101912 A1 * | 5/2008 | Martin et al. ............ 414/935 |
| 2008/0208523 A1 | 8/2008 | Schenck et al. |
| 2009/0118862 A1 * | 5/2009 | Genetti et al. ............ 700/254 |
| 2009/0233515 A1 * | 9/2009 | Kisoda ............ 445/73 |
| 2010/0018330 A1 | 1/2010 | Marty et al. |
| 2010/0193672 A1 * | 8/2010 | Blasenheim et al. ............ 250/234 |
| 2010/0250010 A1 * | 9/2010 | Ferrara et al. ............ 700/279 |
| 2012/0004770 A1 | 1/2012 | Ooyen et al. |
| 2013/0286192 A1 * | 10/2013 | Ramezanifard et al. ..... 348/135 |
| 2014/0005829 A1 * | 1/2014 | Chhatpar et al. ............ 700/254 |

FOREIGN PATENT DOCUMENTS

| | | |
|---|---|---|
| JP | 2002-217598 | 8/2002 |
| JP | 2007033130 | 2/2007 |
| WO | 2011066269 | 6/2011 |

* cited by examiner

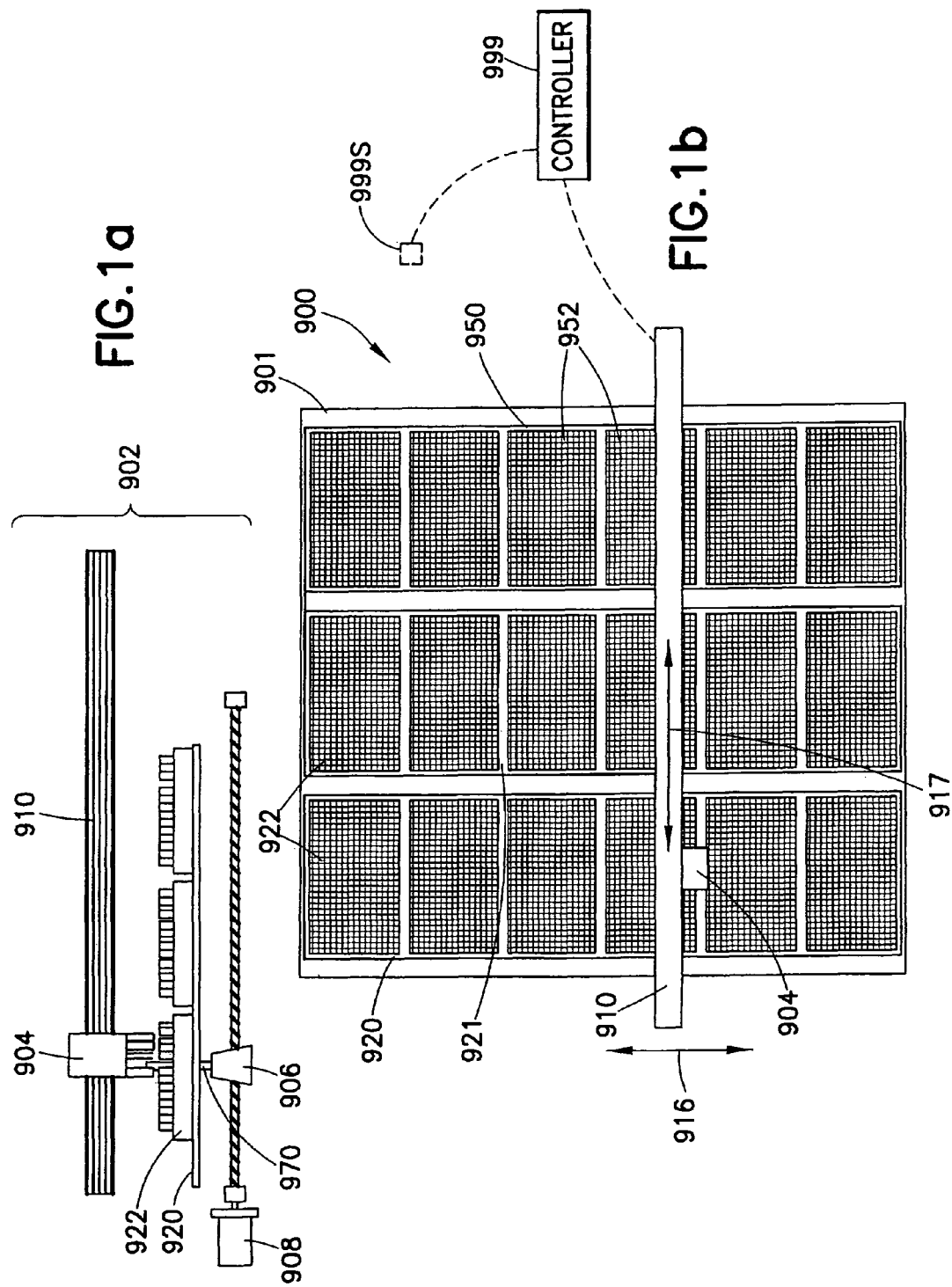

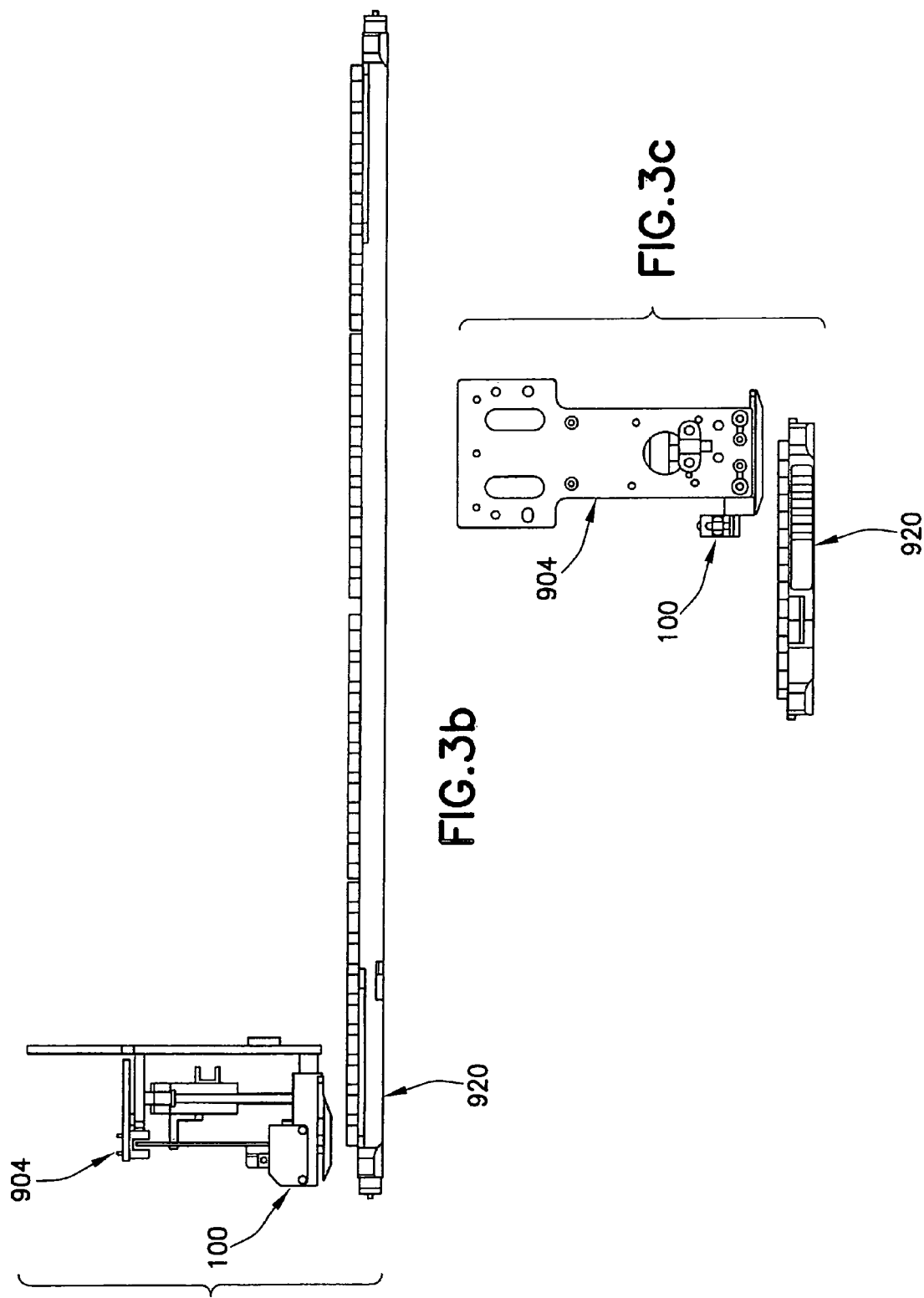

METHOD AND DEVICE FOR COMPENSATION FOR DIMENSIONAL VARIATIONS IN LOW TEMPERATURE SAMPLE GROUP HOLDERS

CROSS-REFERENCE TO RELATED APPLICATIONS

This application is a non-provisional of and claims the benefit of U.S. provisional patent application No. 61/510,455 filed on Jul. 21, 2011, the disclosure of which is incorporated herein by reference in its entirety.

BACKGROUND

1. Field

The exemplary embodiments generally relate to storage and retrieval systems and, more particularly, to automated storage and retrieval systems.

2. Brief Description of Related Developments

Many scientific and medical organizations, including industrial concerns, regulatory agencies, research laboratories, and academic institutions, have the need for secure storage of very large numbers, e.g., millions of samples and specimens. Such fields include pharmaceutical, biotechnology, laboratory diagnostics, genomics, biospecimen, forensic, agrichemical and specialty chemical. Depending on the application, the sample sizes can vary from tens of microliters to several drams, which are stored in small, sealed plastic tubes, vials or multiwell plates. The individual sample containers are retained in a rack that allows individual samples to be inserted or removed without removing an entire rack, or the sample group holder that holds one or more racks, from the system. To extend the useful lifetime of the samples, they are stored in a controlled environment of low temperature (typically −20° to −80° C. or lower), low humidity, and inert gas (nitrogen), and are subjected to as little environmental variation as possible. In order to handle very large numbers of samples in the most efficient manner, a number of considerations must be made to enhance the system's flexibility and adaptability for different applications.

An important component of many such storage systems is a robotic system, e.g., a sample group holder conveyor, for removing and replacing the racks and sample group holders from the storage compartment with minimal impact to the low temperature environment. The sample group holder conveyor delivers sample group holders or racks with selected samples to a controlled environment that is not as cold as the storage compartment, but is at some intermediate temperature between the low or ultra-low temperature of the storage compartment and the laboratory environment to prevent the samples from thawing. This controlled temperature area into which the sample vials are delivered may also be maintained in an inert atmosphere and low humidity environment. Another robotic system that works in cooperation with the sample group holder conveyor is the tube picker, sometimes referred to as the "cherry picker", which allows individual tubes to be extracted from the sample group holder or rack that was retrieved from the storage compartment and placed into a separate sample group holder or rack for processing or analysis. An exemplary vial picker is described in U.S. Patent Publication No. US 2008/0044263, which is incorporated herein by reference in its entirety.

Briefly, the storage system controller, which also controls the sample group holder conveyor and tube picker operation, maintains a database of information about each sample including the location (e.g., shelf or carousel) at which it is stored within the storage compartment and its location within its sample group holder and rack. Once the sample group holder has been removed from the storage compartment and placed on the "pick table", the tube picker moves within an x-y plane to pre-selected positions within the sample group holder that holds the samples to be extracted, which can be referred to as the "source sample group holder". The tube picker includes a pusher mechanism, which lifts the sample containers up and out of the sample group holder, and a pick head, which has one or more cavities for receiving the sample containers that are lifted by the pusher mechanism. The pusher mechanism moves independently from the moveable pick head, allowing the pick head to receive multiple tubes from different locations of a sample group holder. The pick head is then moved to a destination over a destination sample group holder and the ejector mechanism is actuated, placing all tubes in one motion.

The small sizes and close packing of the tubes in the sample group holders means that considerable precision is required when picking the tubes from the sample group holders. The ability to precisely locate each selected tube becomes complicated due to, for example, the thermal effects on the sample group holder material. Specifically, the sample group holders can experience changes in length on the order of several millimeters, which makes it difficult for the picker to find and select the tube if it is a few millimeters away from where it is expected to be.

BRIEF DESCRIPTION OF THE DRAWINGS

The foregoing aspects and other features of the disclosed embodiment are explained in the following description, taken in connection with the accompanying drawings, wherein:

FIGS. 1a and 1b are diagrammatic views (front and top) of the pick table and pick head gantry with holders for source and destination sample groups or arrays in position in accordance with aspects of the disclosed embodiment;

FIGS. 3a-3c are perspective, side and rear views, respectively, of the picker mechanism with a sensor in accordance with aspects of the disclosed embodiment;

DETAILED DESCRIPTION

Figure 2A:
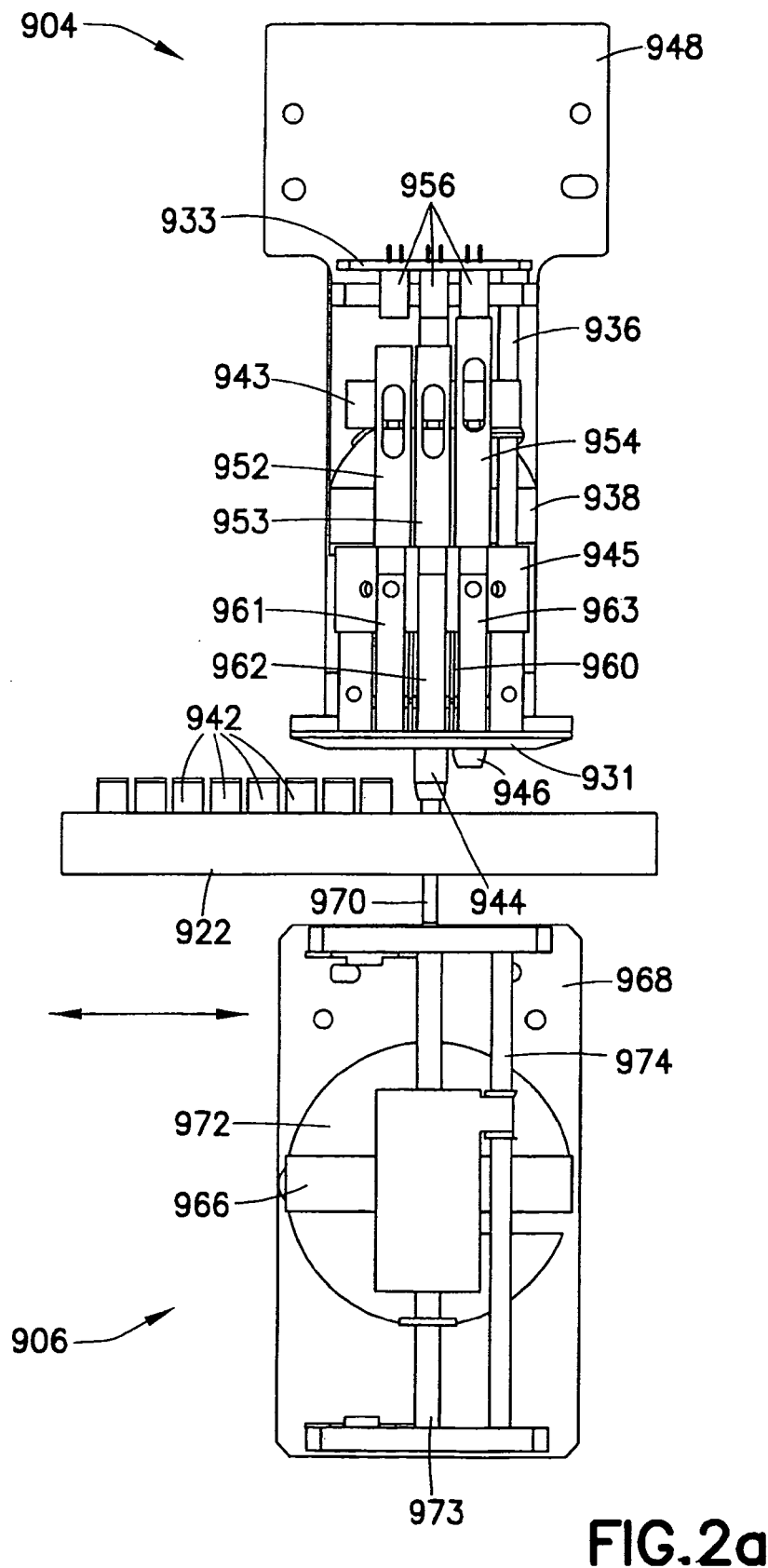
FIGS. 2a-2c are a front, side and perspective views, respectively, of a sample selector mechanism in accordance with aspects of the disclosed embodiment.

Although the aspects of the disclosed embodiment will be described with reference to the drawings, it should be understood that the aspects of the disclosed embodiment can be embodied in many forms. In addition, any suitable size, shape or type of elements or materials could be used.

The aspects of the disclosed embodiment provide a method and device to address the dimensional variations that occur with respect to a location of sample group holders in the storage and retrieval system and/or a location of one or more sample containers held by the sample group holder(s) as the result of, for example, temperature changes, material stresses, tolerance build-ups (for example between components of the storage and retrieval system and/or parts of the sample group holder(s)), interference and/or misalignment between mating components (e.g. interference/misalignment between samples and their respective holding locations within the sample group holders, interference/misalignment between the sample group holders and sample group holder handlers/conveyors), etc. to allow the required precision for rapid, automated sample container selection. It should be understood that while the sample containers are described herein as being tubes, in other aspects the sample containers may have any suitable shape/form. In still other aspects the samples may be uncontained.

According to the aspects of the disclosed embodiment, as will be described in greater detail below, one or more sensors may be placed on, for example, a pick head or at any other suitable location of the storage and retrieval system to locate one or more ends and/or sides of the sample group holder or any other suitable reference datum(s) on the sample group holder. The sensor is movable relative to the pick table or platen on which the sample group holder(s) or tray(s) are placed. Movement of the sensor may be powered by a common motor as the pick head, or the sensor may have an independent drive and motor for moving the sensor relative to the pick table independent of the pick head. It is noted that the term sample group holder, used herein for convenience, may be any suitably sized and shaped holder having a holder frame, also referred to herein as a tray, and may hold one or more groups (or arrays) of sample containers or racks (which hold one or more groups or arrays of sample containers). As noted before, the individual sample containers may be held in the sample group holder in any suitable grouping or arrayed arrangement disposed in a predetermined relationship with the sample group holder. The arrays or groups of sample containers in the sample group holders may be referred to as racks that may be removable from the sample group holder frame as a unit, with the sample container group therein. The one or more sensors may be used to obtain an actual measurement of the sample group holder length and/or width and adjust, within for example, a memory or database of a controller, the expected locations of all the tubes to match the actual locations of the tubes (as opposed to the theoretical locations of the tubes in a sample group holder having nominal dimensions at a predetermined temperature and located at a nominal position). It is noted that the nominal dimensions of the sample group holder may be the dimensions of the sample group holder before, for example, changes in sample group holder dimensions due to thermal expansion/contraction, material stresses, etc. The nominal position of the sample group holder may be a predetermined location of the sample group holder for transferring tubes to and from the sample group holder before, for example, tolerance build-ups, interference and/or misalignment between mating components, etc. The "actual measurements" and "actual location" of the sample group holder may correspond to deviations from the nominal dimensions and nominal position noted above. With respect to temperature, it is noted that because the sample group holder length may change constantly with temperature, the measurement of the sample group holder with the one or more sensors may be repeated at any suitable intervals to adjust the picking/placing locations for dimensional changes as the sample group holder temperature (or the temperature of the controlled environment within which the sample group holder is located) increases or decreases. In one aspect, the sample group holder may be measured (for changes in dimension and/or changes in position) at fixed and/or graduated intervals. In other aspects the measurements noted above may be repeated when a pick is missed or at any other suitable time.

Software within the storage and retrieval system controller 999 uses the above described "actual" measurements and/or location to calculate the spacing of the tubes and/or the locations of the tube centers within the sample group holder and, based on the calculated spacing/locations, moves the pick head to the current or actual location of the target sample or tube.

The tube picker sensor according to aspects of the disclosed embodiment provides significant improvement with systems that store samples at −20° C., and is essential for −80° C. systems, where the sample group holders are stored at −80° C. and picked at −20° C.

FIGS. 1a and 1b illustrate the picker mechanism 902 that is utilized in a representative cherry picker module 900 of a sample storage and retrieval system in accordance with an aspect of the disclosed embodiment. In one aspect the cherry picker 900 is configured to pick and place tubes while in other aspects the cherry picker 900 may be configured to pick and place any suitable sample container or uncontained sample. The picker module 900 has, for example one or more (in the illustrated example there are two) source sample group holder positions 920, 921 and one (or more) destination sample group holder position 950, which hold multiple sample racks 922 and 952, respectively. The sample group holders are supported on a stationary surface, or "pick table" 901, while the picker mechanism moves within an x-y plane to access different locations on the sample group holders to perform the desired transfer operations. While samples are being extracted from one source sample group holder position, a different source sample group holder can be moved into the other source sample group holder position, allowing for virtually continuous sample selection.

A representative picker mechanism 902 includes a rail 910, a pick head 904 and a pusher mechanism 906. The representative picker mechanism 906 illustrated in the Figs. is exemplary and in other aspects the picker mechanism may have any suitable configuration including, for example, an articulated arm robot such as a SCARA (selective compliant articulated robot arm) configuration or a "frog leg" arm disposed to movably position a pick head to pick and place sample containers from and to the sample group holder(s). The rail 910 may be drivingly mounted on a linear translator (not shown) that includes one or more tracks along which rail 910 rides on for movement along one axis 916 (the y-axis in FIG. 1b). As may be realized, the linear translator and rail 910 may form a gantry system allowing movement of the pick head 904. Pick head 904 may be drivingly mounted on the rail 910 and be configured to translate along the other axis 917 (x-axis in FIG. 1b) along rail 910. It is noted that the movement of the rail 910 along axis 916 and movement of the pick head 904 along axis 917 may be effected by any suitable drive. The positioning of pusher mechanism 906 may be controlled in one or more of the axes 916, 917 by any suitable drive or translator 908 such as a screw drive.

Pusher mechanism 906 may also include a Z-motion drive configured to move a pusher rod 970 for lifting the sample containers up and out of the racks 922, pushing them into one or more cavities in pick head 904 as will be described in greater detail below. In one aspect, the pusher mechanism 906 moves independently from pick head 904, allowing the pick head to receive multiple tubes from different locations of a sample group holder substantially without pick head movement (e.g. where the pick head 904 includes multiple cavities having substantially the same spacing as the holding locations of the sample group holders, the pusher rod 970 may be aligned with each of the cavities by moving the pusher mechanism 906 for lifting tubes into the cavities substantially without moving the pick head 904). Once the cavity or cavities in the pick head 904 are full, pick head 904 is moved to a destination over a rack 952 in destination sample group holder 950, where an ejector mechanism of the pick head 904 is actuated, placing all sample containers carried by the pick head 904 in the rack 952 in one motion.

Figure 2B:
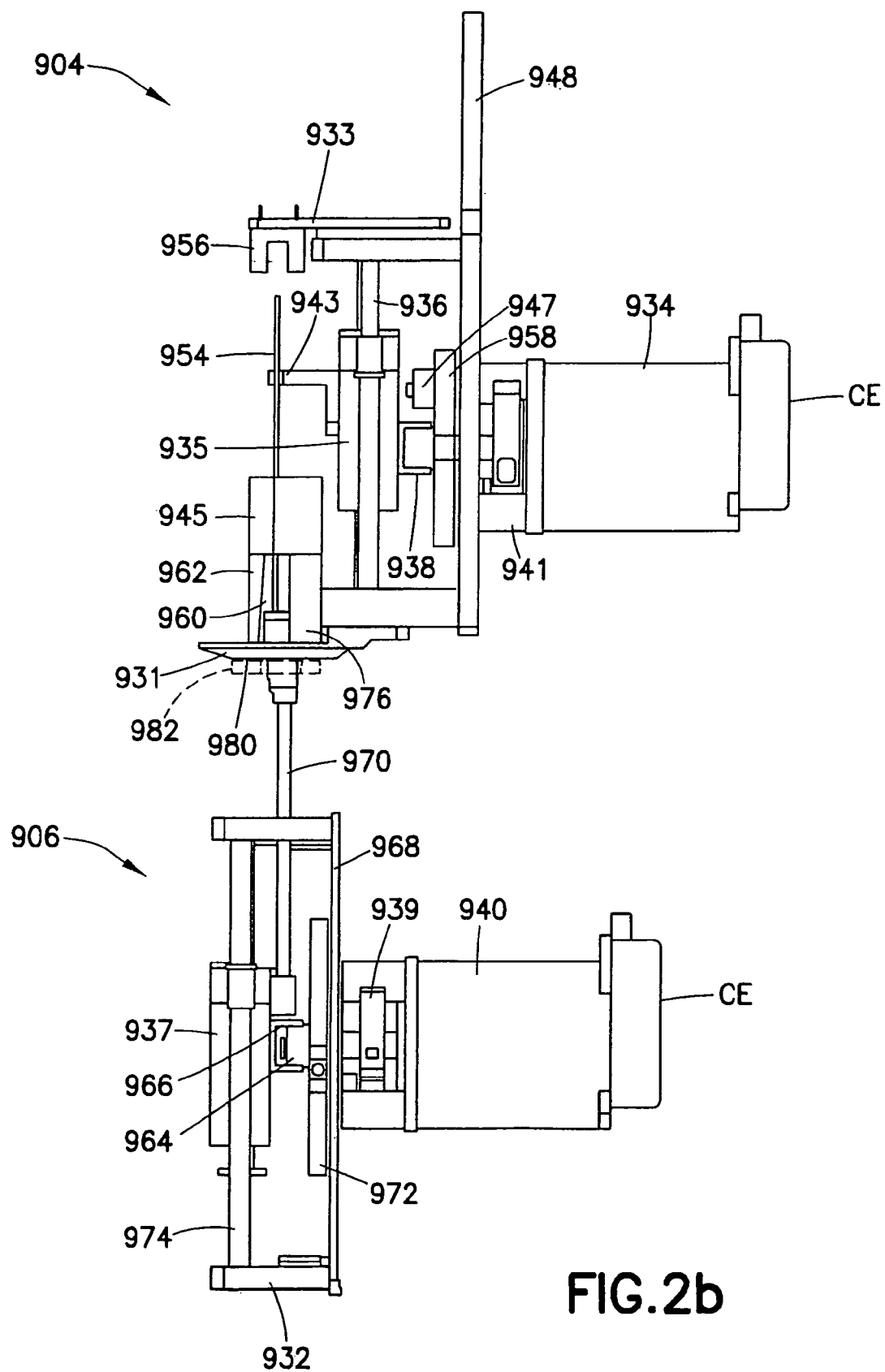
Figure 2C:
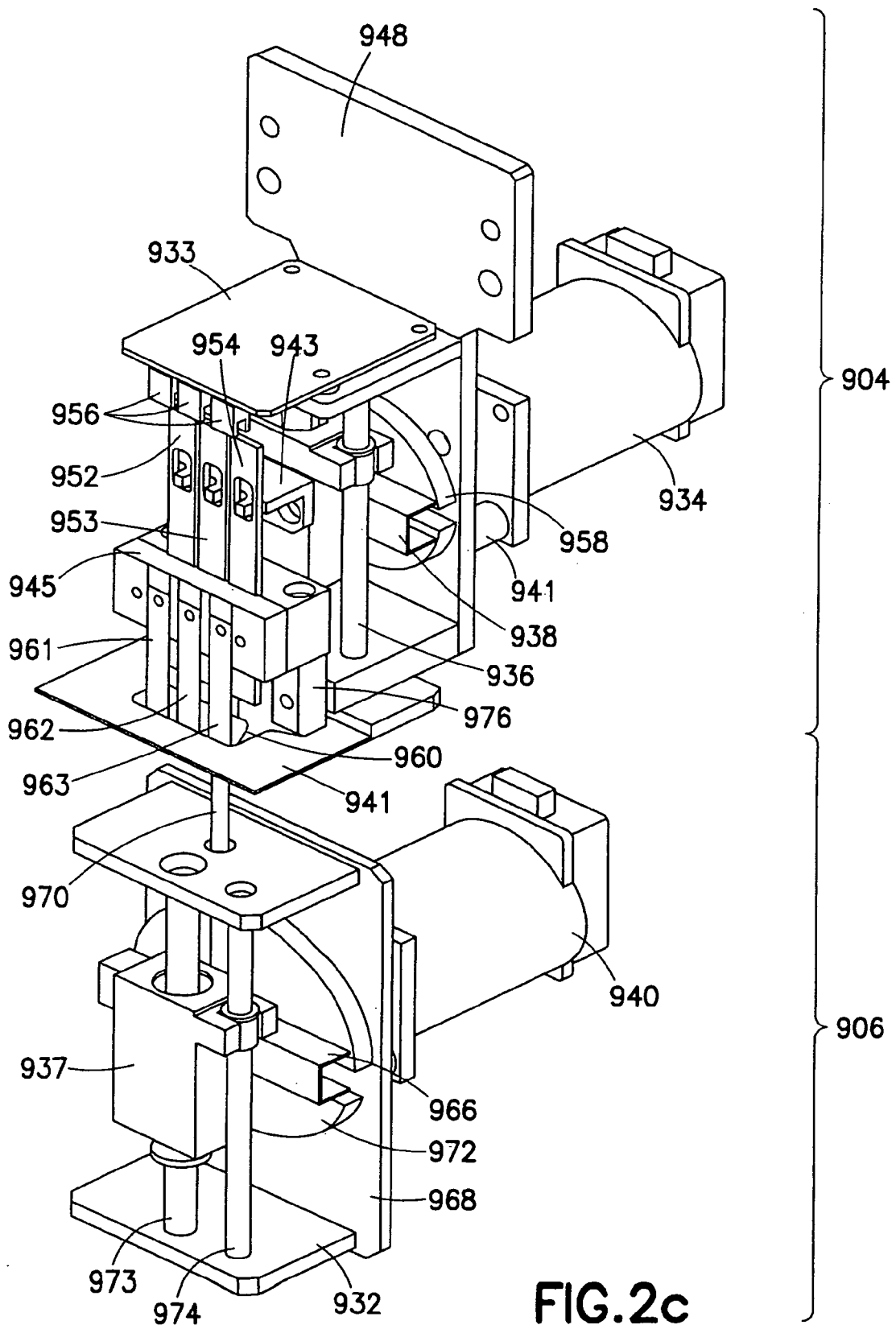

FIGS. 2a-2c illustrate the elements of the pick head 904 and pusher mechanism 906. Pick head 904 is mounted on rail 910 (FIGS. 1a and 1b) in any suitable manner such as by way of mounting plate 948. The mounting plate 948 also provides the frame for attachment of the pick head components. Pick head bottom plate 931 is mounted to a portion of the frame that extends perpendicular to mounting plate 948 and has an opening through which the sample containers pass. Bottom plate 931 will generally be located a short distance above the rack 922 from which the samples are being picked. When the picker mechanism 902 is also being used to separate tubes that have been sealed with an adhesive sheet, as described below, bottom plate 931 may come into substantial contact with the top surface of the rack 922. Just above bottom plate 931 are springs 961-963 which are releasably attached to block 945 (which may be attached to the frame) such that the springs 961, 963 extend downward, e.g., towards the rack 922. Each spring 961-963 is formed from a resilient metal or other suitable resilient material and has an inwardly extending tapered tooth that causes the spring to cam outward when a sample container is pressed upward against the tooth. The inner surface of each spring 961-963, the lower surface of block 945, and back wall 976 define a cavity 960 having one or more sample container holding locations within which one or more sample containers 942, 944, 946 can be retained during the picking process. The size of the cavity, which may be defined by the length of springs 961-963 between the upper edge of the tapered tooth and the bottom surface of block 945, should closely fit the size of the sample container in order to ensure proper operation. The springs 961-963 may be removable to allow for handling different length sample containers. For example, when different length sample containers are to be handled, the springs 961-963 may be removed by unscrewing the spring screws and may be replaced with springs that have lengths corresponding to the sample containers to be handled. The spring retains its associated sample container within cavity 960 until the sample container is ejected.

Sensor/ejector blades 952-954 are slidably mounted to the frame and extend through slots in block 945 so that when a sample container 942, 944, 946 is pushed into cavity 960, the blade 952-954 above the sample container 942, 944, 946 is pushed upward so that the upper end of the blade is positioned for detection by one of a set of optical detectors 956 that are mounted on a printed circuit board 933 above block 945. (PCB 933 may provide an electrical or any other suitable wired or wireless connection to the picker controller 999 (FIG. 1b).) Activation of the optical sensor 956 produces a signal that tells the picker controller 999 that a sample container 942, 944, 946 is retained within a given slot in the pick head 904. As illustrated in FIG. 2a, sample container 946 is retained within cavity 960, thus pushing blade 954 upward where its upper end is detected by optical sensor 956. Sample container 944 is in the process of being pushed up against the tapered tooth of spring 962 by pusher rod 970. The top of sample container 944 will contact with the lower edge of blade 953 to push it upward where it, too, will be detected by the corresponding optical sensor 956. In one aspect, the pick head 904 is configured for accepting three sample containers, as there are three springs 961-963, three blades 952-954 and three optical sensors 956. In other aspects the pick head 904 may be configured to hold any suitable number of sample containers. In one aspect once all optical sensors 956 have detected the presence of a sample container in the cavity 960, the picker controller 999 directs the pick head 904 to move to a position of a destination rack 952 in the destination sample group holder 950 (FIG. 1b) into which the sample containers 942, 944, 946 are to be placed. Once the pick head 904 is in position over destination rack 952, cam motor 934 of the pick head is activated to rotate flywheel 958, causing cam wheel 947 to apply a downward force against channel 938. Channel 938 is attached to the back side of pick head slide 935, causing slide 935 to move downward along guide 936. Extending from the front side of slide 935 is ejector bar 943, which has an ejector tab that extends through a slot in each of blades 952-954. As slide 935 moves downward, ejector bar forces blades 952-954 downward against the tops of the sample containers 942, 944, 946 in cavity 960, ejecting them simultaneously from the pick head 904 and into the destination rack 952. Flywheel 958 can be weighted to provide additional inertia upon activation to ensure that it follows its full cycle.

While the above describes a pick head 904 adapted for receiving three sample containers, it will be readily apparent, as noted above, that more or fewer sample containers can be handled by providing from one cavity-spring-blade-sensor combination to many such combinations as may be practical for efficient operation.

Pusher mechanism 906 cooperates with pick head 904 by driving pusher rod 970 upward, through e.g. the open bottoms of sample group holder 920 and rack 922 to lift the sample container 942, 944, 946 up and push it upward against the toothed springs 961-963 of the pick head 904. Pusher mechanism 906 may be attached to translator 908 via mounting plate 968 to permit independent movement of the pusher mechanism 906 and pick head 904. Pusher rod 970 is attached to pusher slide 937 which moves vertically along column 973 and is stabilized by pusher guide 974. The column 973 and pusher guide 974 may both be attached to base 932. Vertical motion of the pusher rod 970 may be initiated by a similar cam mechanism as that described above for the pick head ejector. For example, cam motor 940 rotates flywheel 972, which moves cam wheel 964 within channel 966 to apply upward or downward force against the channel 966. Channel 966, which is attached to the back side of pusher slide 937, causes pusher rod 970 to move up or down, depending on the direction of rotation of flywheel 972. As with the pick head 904, flywheel 972 can be weighted to ensure that it produces sufficient inertia to complete its full cycle. Pusher rod 970 may be removable and in one aspect can be replaced with different length rods as may be needed for handling different length sample containers.

Each of cam motor assemblies 934, 940 includes a magnetic position sensor 941 or 939, respectively, which provides feedback on the position of the corresponding flywheel 958 or 972 to ensure that the flywheel is rotated through its full cycle. In one aspect control electronics may be located within the boxes CE attached to the ends of the motors 934, 940. In one aspect, as noted above, pick head 904 can be modified to perform the function of die cutting, thus eliminating the need for an additional step, and additional instrumentation, for separating sample containers within a sample rack such as sample rack 922 that have been sealed with a single sheet of foil or polymer (e.g. a sample container seal). In this aspect, a cutting plate 980 is affixed to, for example, the bottom of pick head bottom plate 931 (or any other suitable location of the pick head 904) with cutting edge 982 aligned with the bottom of cavity 960. Cutting plate 980 can be formed from any suitable material such as, for example, aluminum or stainless steel. Cutting edge 982 need not be intentionally sharpened since the normal process of machining the plate to form the opening by cutting or drilling produces a sharp enough edge to cut the seal around the perimeter of the sample container when it is pushed upward by the pusher mechanism. This allows the sample containers 942, 944, 946 to be stored with the seal intact until needed. Typically only a few samples are needed at a time, so the seal is cut only around the sample containers 942, 944, 946 of the samples that are desired when they are prepared for selection.

Figure 3A:
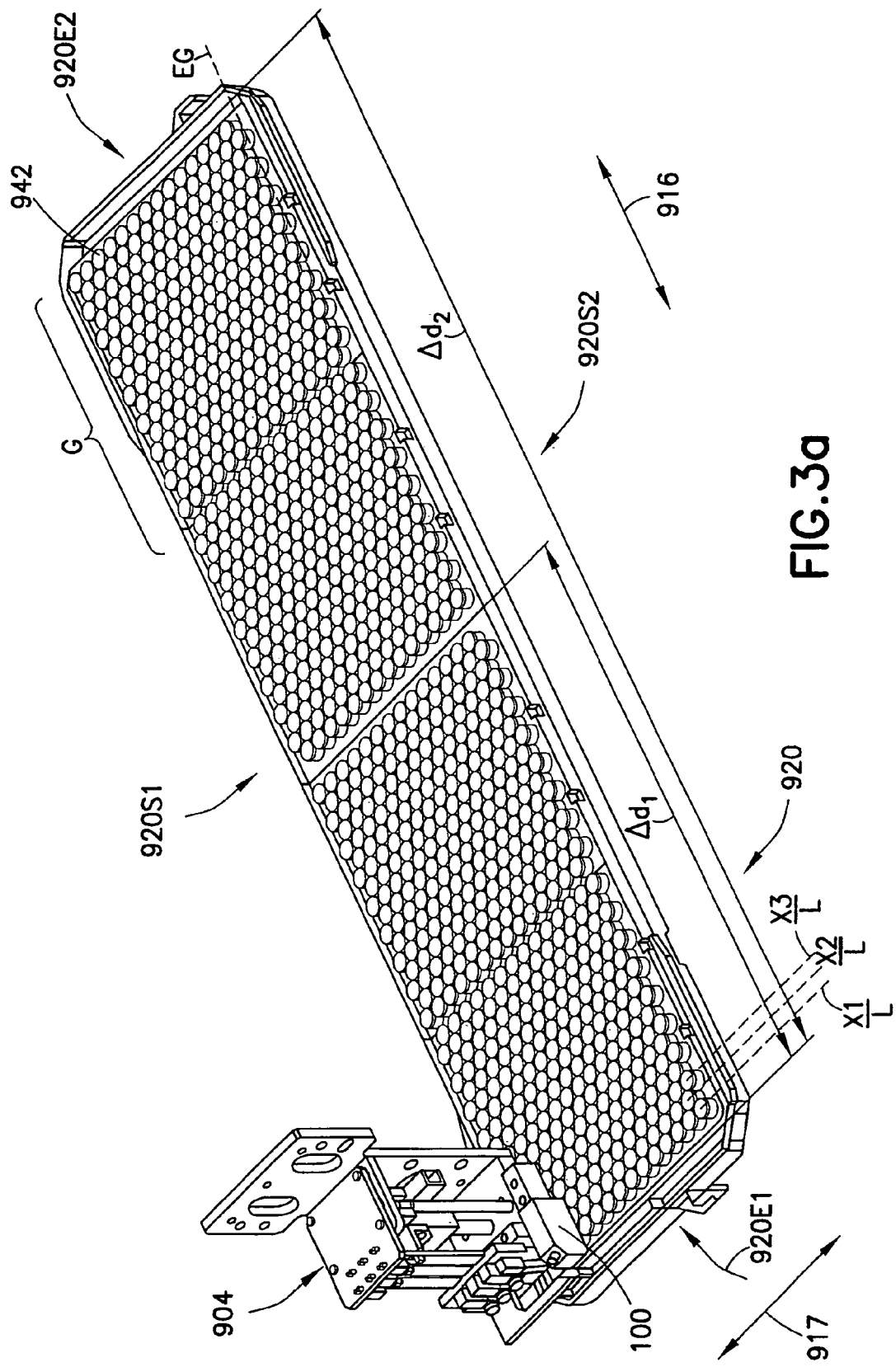

FIGS. 3a-3c show the pick head 904 positioned over the source sample group holder 920. It is noted that the configuration shown in FIGS. 3a-3c is representative and in other aspects the sample storage and retrieval system may have any suitable configuration. Any suitable sensor 100 (e.g. such as one or more of a CCD camera, an optical detector, a reflective beam sensor, a proximity detector, etc.) may be mounted on the pick head 904 in any suitable manner to allow the sensor to detect, for example, the edges (e.g. one or more of the end 920E1, 920E2 and side 920S1, 920S2 edges) of the sample group holder 920 (or one or more edges of one or more racks 922, 952 within the sample group holders). In other aspects, the sensor 100 may detect any suitable reference datum(s) on the sample group holder 920. In still other aspects the sensor 100 may detect the edge EG of one or more sample containers and/or an edge or boundary of a grouping G of sample containers 942 and/or detect features such as any suitable points (e.g. 2 or 3 or more points) or sections that define an edge or boundary (e.g. so that a line formed by the edges can be determined). In the illustrated example, sensor 100 is shown mounted on the side of the pick head 904 but in other aspects the sensor 100 may be mounted to the pick head 904 at any suitable location or be mounted independent of the pick head so as to be movable independent of the pick head. The sensor 100 may be operatively connected in any suitable manner to, for example, any suitable controller such as controller 999 for sending one or more edge detection signals to the system controller 999. As noted above, the sensor 100 along with the system controller 999 may form a compensation system for determining the actual dimensions and/or actual location of the sample group holder 920 and the sample containers held therein where the system controller 999 is configured to determine the locations of the sample containers from the one or more edge detection signals as will be described below.

Figure 4A:
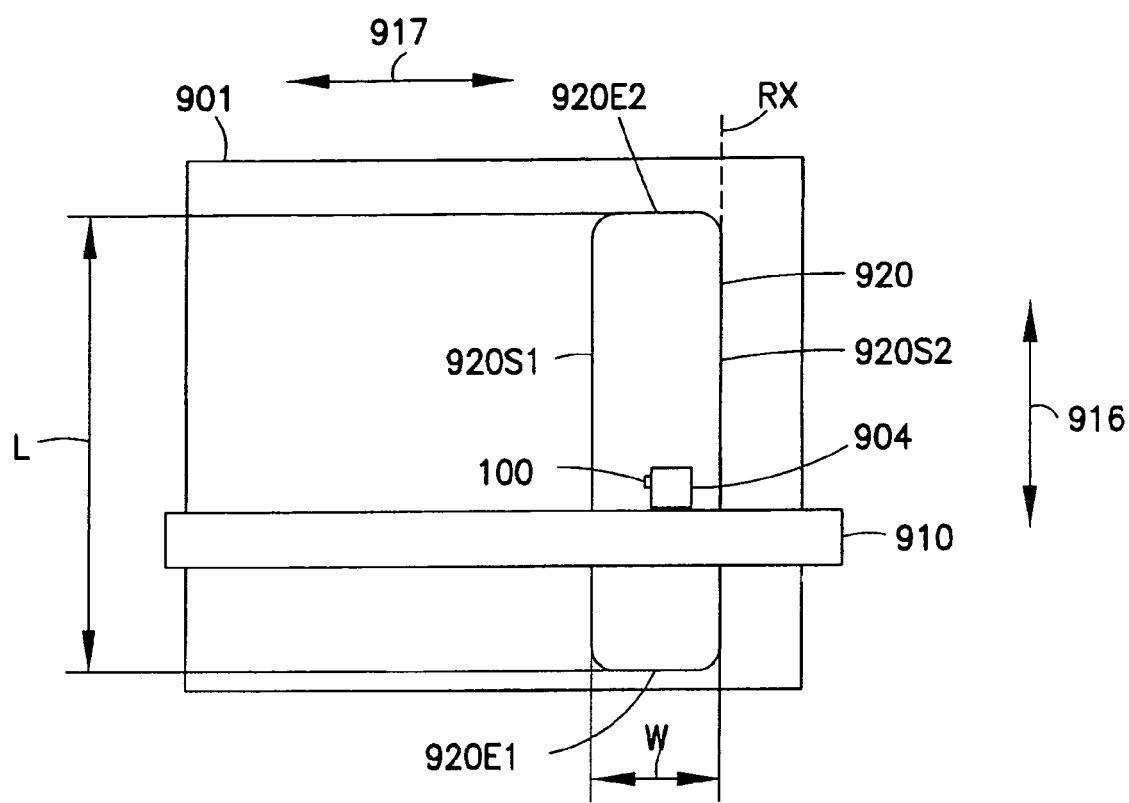
FIGS. 4a-4d illustrate steps in the sequence for measuring and compensating for changes in the sample group holder length and/or position in accordance with aspects of the disclosed embodiment.
Figure 4B:
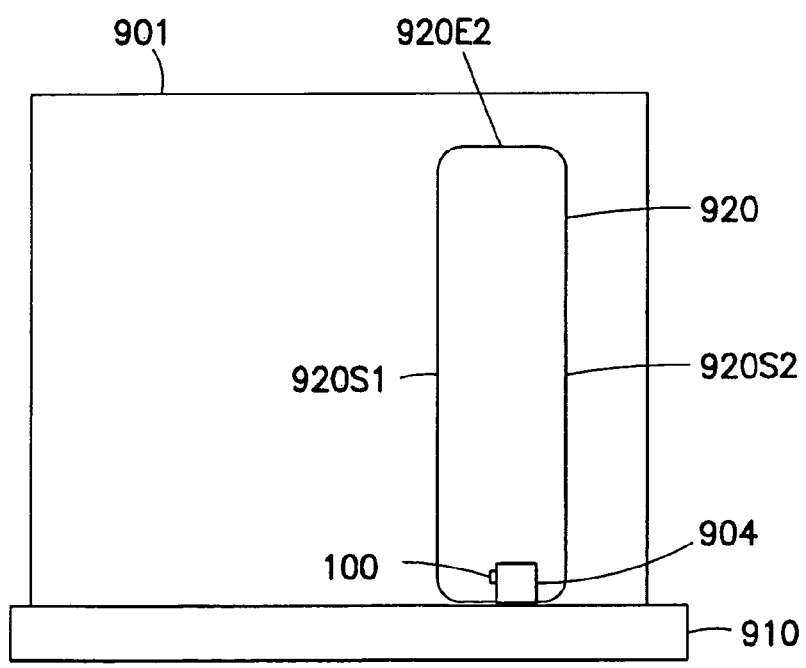
Figure 4C:
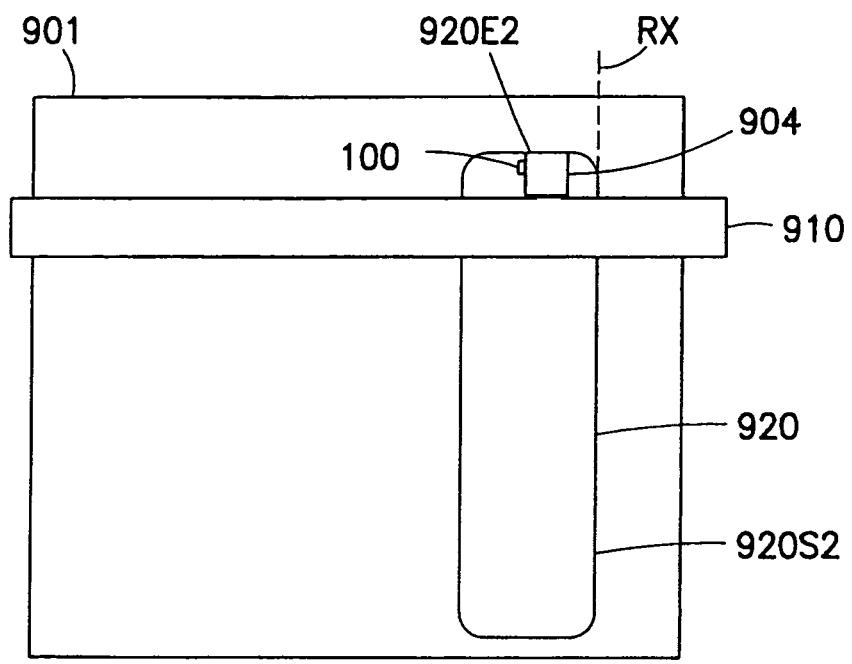

FIGS. 4a-4c illustrate a sequence of the operation of the compensation system. As noted above, the actual position and/or dimensions of a sample group holder 920 on the pick table 901 may differ from a nominal or expected position and/or dimensions of the sample group holder 920 on the pick table for any suitable reason such as, for example, temperature changes, material stresses, tolerance build-ups (for example between components of the storage and retrieval system and/or parts of the sample group holders), interference and/or misalignment between mating components (e.g. interference/misalignment between samples and their respective holding locations within the sample group holders, interference/misalignment between the sample group holders and sample group holder handlers/conveyors), etc. The compensation system may be configured to obtain one or more measurements of the sample group holder for compensating for these dimensional variances. FIG. 4a shows pick table 901 with the source sample group holder 920 in position after delivery by the sample group holder conveyor (not shown). The gantry system and pick head 904 may be positioned at a starting position over the top of the sample group holder 920 for detecting a predetermined feature of the sample group holder 920. The starting position may be any suitable predetermined location such as an end or edge of the sample group holder or at a reference datum of the sample group holder. In one aspect, for exemplary purposes only, the predetermined feature at the starting position may be end 920S1 of the sample group holder 920 but in other aspects the predetermined feature may be any suitable feature of the sample group holder (e.g. any suitable side or reference datum of the sample group holder, an edge of one or more sample containers or one or more edges of the racks located in the sample group holder, an edge or boundary of a group of sample containers, etc.).

FIG. 4b shows the rail 910 of the gantry system moved to the end 920E1 of the sample group holder 920 where the sensor 100 detects or otherwise looks for e.g. the edge at the end 920E1 of the sample group holder 920. The position of the edge at the end 920E1 of the sample group holder 920 may be transmitted to the system controller 999 for use in calculating the length L of the sample group holder due to, for example, linear thermal expansion. In one aspect, the rail 910 may move to the other end 920E2 of the sample group holder 920 where the sensor 100 detects or otherwise looks for the edge of the sample group holder 920 at the end 920E2 as shown in FIG. 4c. The position of the edge at the end 920E2 of the sample group holder 920 may also be transmitted to the system controller 999 for use in calculating the length L of the sample group holder due to, for example, linear thermal expansion. The system controller 999 may determine the actual length of the sample group holder from the measured locations of the edges at ends 920E1, 920E2 of the sample group holder and compare the actual length of the sample group holder 920 with a nominal length of the sample group holder for determining an adjustment or offset value in direction 916 for determining, for example, the location of the sample containers 942 within the sample group holder 920.

In another aspect, the system controller 999 may be configured to determine the locations of the sample containers in, for example, direction 916 substantially directly from the measured length L of the sample group holder. For example, referring also to FIG. 3A, a predetermined relationship between the sample containers and, e.g., a nominal length of the sample group holder 920 may be known (e.g. each row of sample containers in, for example, the direction 916 may be located at a predetermined percentage of the nominal sample group holder length away from, for example, the edge of end 920E1). The system controller 999 may control the gantry system so that the position of the edges at ends 920E1 and 920E2 are determined. The system controller 999 may be configured to determine the locations of each row of sample containers 942, at least from the end 920E1, based on the measure length L of the sample group holder 920 and percentage length of each row. For example, a first row of sample containers may be located a percentage X1/L from the edge at end 920E1, a second row of sample containers may be located a percentage X2/L from the edge at end 920E1, a third row of sample containers may be located a percentage X3/L from the edge at end 920E1, etc. and because the measured length L of the sample group holder is known the controller may use the percentage lengths to determine the "actual" location of the sample containers in the direction 916 in any suitable manner.

As may be realized, the pick head 904 may also be moved so that the sensor may detect or otherwise look for the edge at each of the sides 920S1, 920S2 in a substantially similar manner to that described above for determining the actual width W of the sample group holder 920 such that, in one aspect, the system controller 999 compares the actual width W of the sample group holder 920 with a nominal width of the sample group holder for determining an adjustment or offset value in direction 917 for determining the location of the sample containers. In other aspects the system controller 999 may determine the location of the sample containers substantially directly from the measured width W of the sample group holder and a percentage width of each row of sample containers in a manner substantially similar to that described above.

In other aspects, the system controller may determine the actual length L and width W from only two points on the sample group holder, e.g., such as by detecting suitable features at opposite corners of the sample group holder 920.

In still other aspects, the system controller 999 may be configured to determine the length L of the sample group holder using two or more dimension measurements $d_{1m}$, $d_{2m}$ so, for example, tolerance buildup in the sample group holder may be substantially eliminated during the determination of the length of the sample group holder. For example, referring to FIG. 3a:

$$\Delta d_1 = \Delta d_2/2 \text{ and} \qquad [\text{eq. 1}]$$

$$d_{1m} = d_{2m}/2 \qquad [\text{eq. 2}]$$

where $\Delta d_1$ and $\Delta d_2$ are the changes in dimensions of the sample group holder 920 due to, for example, temperature changes or any other suitable variance as noted above. Dimensions $d_{1m}$ and $d_{2m}$ are nominal dimensions of the sample group holder 920. Further, $$\Delta d_1 = d_{1mt} - (d_{1m} + V/2) \text{ and} \qquad [\text{eq. 3}]$$

$$\Delta d_2 = d_{2mt} - (d_{2m} + V) \qquad [\text{eq. 4}]$$

where $d_{1mt}$ and $d_{2mt}$ are measurements of the sample group holder 920 that correspond to $d_{1m}$ and $d_{2m}$ at time t and V is the variance in the sample group holder. As may be realized, one of equations 3 and 4 may be solved for the variance V and substituted into the other of equations 3 and 4 for determining, for example, $\Delta d_2$ using one or more of equations 1 and 2.

In other aspects the length L and/or width W of each sample group holder may be measured upon insertion of the sample group holder 920 (e.g. at time $T_0$) into the sample storage and retrieval system. The length L and/or width W of the sample group holder may be measured at later times, such as time $T_1$ and time $T_2$ so that the change in length L of the sample group holder 920 at time $T_1$ or $T_2$ can be determined by subtracting, for example, the length L at $T_0$ from the length L at time $T_1$ or time $T_2$. Similarly the change in width W of the sample group holder 920 at time $T_1$ or $T_2$ can be determined by subtracting, for example, the width W at $T_0$ from the width W at $T_1$ or $T_2$.

The system controller 999 may insert one or more of the adjustment values in the directions 916, 917 (e.g. the x and y directions) into the instructions for locating the actual position of the target tube or sample container and move the pick head 904 into position over the adjusted x, y coordinate of the target tube. In one aspect one or more of the x and y offset values can be assumed to be uniform along the length of the sample group holder, while in other aspects any suitable algorithm can be used to determine one or more of the x and y offset values of any given position on the sample group holder based on its distance from any suitable reference location of the sample group holder 920, such as for exemplary purposes only, the end 920E1 or side 920S1 (e.g. the starting point of the length or width measurement determination). In one aspect, the process of calculating the length L and/or width W of the sample group holder 920 can be repeated after the initial measurement at fixed intervals or graduated intervals, for example, where more frequent measurements may be performed as time passes and e.g. the temperature change of the sample group holder 920 occurs more rapidly. In other aspects, after the initial measurement, the process of measuring and calculating the sample group holder 920 length L and/or width W can be deferred until the pick head fails to pick up a tube due to an offset from the expected position or at any other suitable time. At that point, the measurement and compensation calculation can be repeated.

Figure 4D:
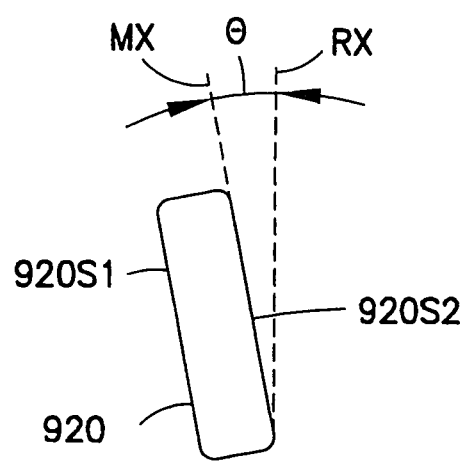

As may be realized, compensation system may also determine if a sample group holder 920 is skewed on the pick table 901 and rotate or otherwise adjust a reference frame of the sample group holder 920 within the controller to allow for picking and/or placing of the tubes or sample containers. For example, referring also to FIG. 4d, the pick head 904 may be positioned so that the sensor 100 detects at least two points on a single or common side 920S1, 920S2 (or end 920E1, 920E2) of the sample group holder 920. The sensor 100 may transmit the positions of the at least two points to the system controller 999 for use in calculating an actual axis MX of the sample group holder 920. The system controller 999 may determine the actual axis MX of the sample group holder 920 from the measured positions of the at least two points and compare the actual axis MX of the sample group holder 920 with a nominal or expected axis RX of the sample group holder 920 on the pick table 901 for determining an adjustment or offset value θ. The system controller 999, using the offset value θ alone or in combination with the positional information determined above (e.g. the actual locations of the ends and/or sides of the sample group holder and/or the x and y offsets) with respect to the x and y offset, may rotate the coordinate system or reference frame of the sample group holder 920 within the controller for enabling movement of the pick head 904 so that the x and y movements of the pick head 904 correspond to the locations of the tubes or sample containers in the skewed sample group holder 920.

Figure 5:
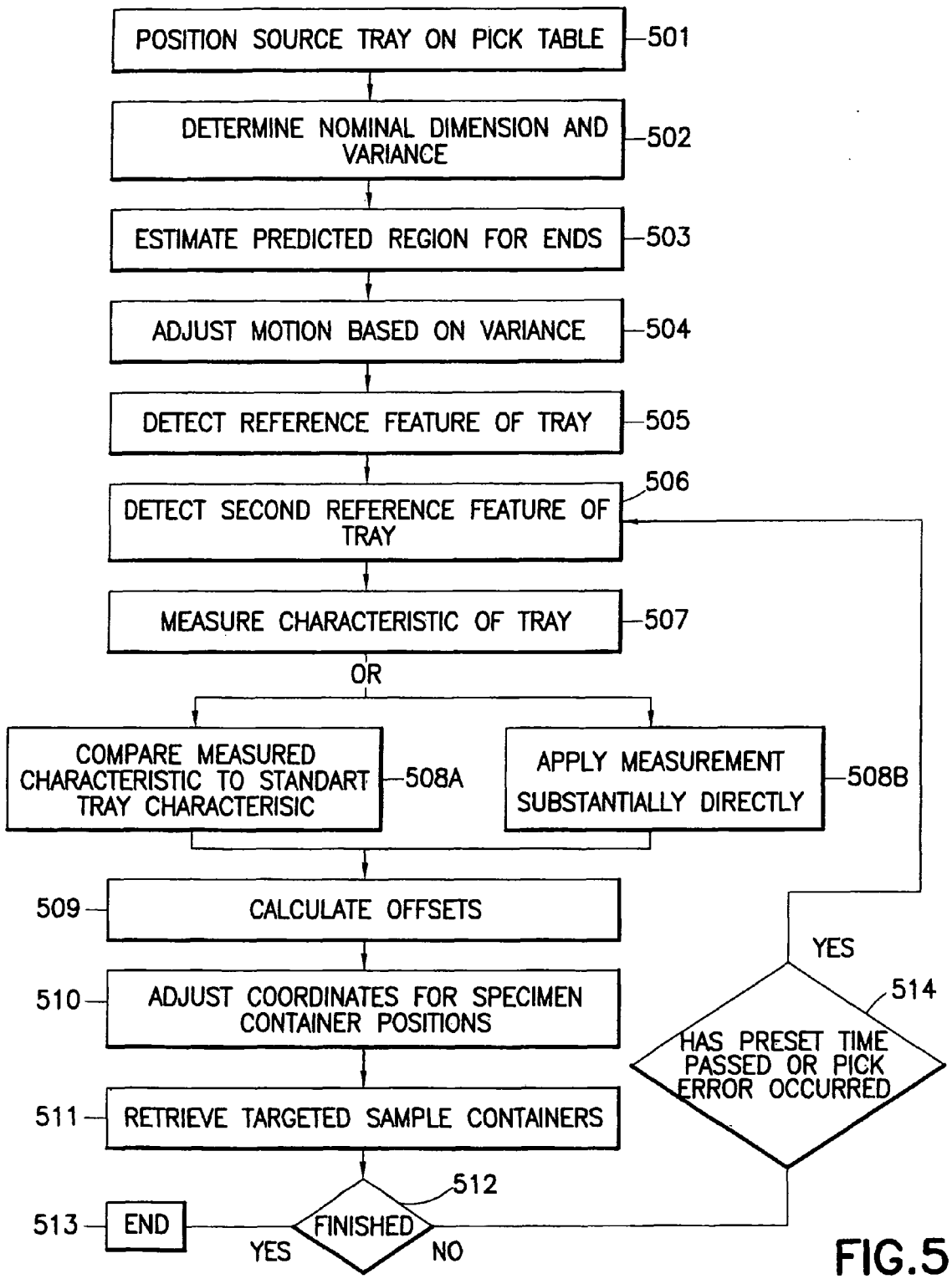
FIG. 5 is a flow chart showing an exemplary process that may be used in measuring and calculating the sample group holder length and/or position and position offsets in accordance with aspects of the disclosed embodiment.

FIG. 5 is a flow chart showing an exemplary process that may be used in measuring and calculating, for example, the sample group holder length, width, position and/or orientation and position offsets. Referring also to FIGS. 4a-4c, in block 501, the process is started by placing or otherwise positioning a retrieved sample group holder 920 on the pick table 901. The nominal dimensions and variance of the sample group holder 902 may be determined in any suitable manner such as by, for example, looking up the nominal dimensional and variance of the sample group holder 902 in a memory of the system controller 999 or by measuring the sample group holder when the sample group holder is inducted into the storage and retrieval system (FIG. 5, Block 502). The system controller 999 may estimate predicted regions of the pick table where the ends 920E1, 920E2 of the sample group holder 920 are expected to be (FIG. 5, Block 503) and may adjust the motion of the gantry system based on an estimated variance in sample group holder position from a nominal position of the sample group holder on the pick table 901 (FIG. 5, Block 504). In block 505, the gantry system is moved so that the sensor 100 on the pick head 904 is moved to any suitable initial reference position over the sample group holder such as the edge of the sample group holder at end 920E1 or any other suitable reference datum so that the edge is detected. In this aspect, this reference position will be used in the measurement of, for example, the sample group holder length L while in other aspects the reference position may be used to determine sample group holder position, misalignment and/or orientation as noted above. In block 506, the gantry system is moved so that the sensor 100 on the pick head 904 is moved to a second position of the sample group holder 920 such as the other end 920E2 of the sample group holder until the sensor detects a feature of the sample group holder 920 at the second position such as, for example, the edge of the sample group holder at end 920E2 or any other suitable reference datum. Once, for example, the features of the sample group holder at the initial and second positions of the sample group holder 920, such as the edges at ends 920E1, 920E2, are detected any suitable characteristic of the sample group holder 920, such as the sample group holder length L, the sample group holder width W, the sample group holder orientation (e.g. e rotation of the sample group holder—FIG. 4d) and/or the sample group holder position (x and/or y position of the sample group holder on the pick table 901), from the reference point may be determined as described above (FIG. 5, block 507). In one aspect, the system controller 999 may include any suitable programming and structure (e.g. processors, memory, etc.) and be configured to compare, for example, the measured characteristic, such as the measured length L, the measured width W, the measured position and/or the measured orientation of the sample group holder against a standard or nominal sample group holder length L, width W, position and/or orientation which has been used to identify the locations of the various tubes in the sample group holder (FIG. 5, block 508A). In other aspects, the system controller 999 may include any suitable programming and structure (e.g. processors, memory, etc.) and be configured to apply the measured characteristic substantially directly (e.g. without a comparison to a nominal sample group holder characteristic) to identify the locations of the various tubes in the sample group holder as described above (FIG. 5, Block 508B). In still other aspects, the measurements at time $T_i$ (i.e. the current time) may be compared to the measurements at a previous time $T_{i-1}$ for determining the offsets. In block 509, the offsets in one or more of the x, y and θ directions are calculated to determine how much, for example, the length L and/or width W of the sample group holder has expanded or contracted due to thermal effects. In other aspects, as noted above, offsets for sample group holder position on the pick table 901 and/or orientation may be calculated. The offset for the tube position of the targeted tube is calculated and adjusted coordinates are provided to the gantry system to move the pick head 904 into position to access the target tube(s) (FIG. 5, block 510). In block 511, the target tube(s) are picked up by the pick head 904 and moved to the destination sample group holder 950 (FIG. 1b). In block 512, if all of the target tubes have been retrieved, the process of retrieving target tubes from the retrieved sample group holder 920 is finished (FIG. 5, block 513) and a new sample group holder is retrieved. If the process is not finished and additional tubes are to be selected from the same sample group holder, in block 514, the system controller 999 will determine whether a preset or otherwise predetermined time has passed over which a significant change in, for example, the sample group holder length L and/or width W might have occurred due to, for example, thermal changes. In other aspects the system controller 999 may be operably connected to a thermal sensor 999S configured to detect a temperature of the sample group holder and/or an ambient temperature of the controlled environment in which the sample group holder is located. The thermal sensor 999S may be any suitable thermal sensor such as, for example, an optical pyrometer. The thermal sensor 999S may detect when a predetermined change in temperature has occurred and send a detection signal to the controller 999 to initiate re-measurement of the sample group holder. If the preset time has passed since the last measurement and/or the predetermined change in temperature is detected, the measurement and calculation blocks 505-510 will be repeated before attempting to retrieve the next tube. Alternatively, if an error has occurred in picking the last tube, blocks 505-510 will be repeated.

In accordance with one or more aspects of the disclosed embodiment an apparatus is provided. The apparatus includes a pick head configured to transfer sample containers to and from a sample group holder, at least one sensor connected to the pick head and configured to detect at least one predetermined feature of the sample group holder, and a controller configured to receive a detection signal from the at least one sensor corresponding to detection of the at least one predetermined feature, determine a change in a predetermined characteristic of the sample group holder based on a detected position of the at least one predetermined feature, and determine a location of one or more samples in the sample group holder to allow for the transfer of the one or more sample containers to and from the sample group holder based on the edge detection signal.

In accordance with one or more aspects of the disclosed embodiment the change in a predetermined characteristic of the sample group holder is a change in length from a nominal length of the sample group holder.

In accordance with one or more aspects of the disclosed embodiment the change in a predetermined characteristic of the sample group holder is a change in width from a nominal width of the sample group holder.

In accordance with one or more aspects of the disclosed embodiment the change in a predetermined characteristic of the sample group holder is a change in position from a nominal position of the sample group holder on a pick table of the apparatus.

In accordance with one or more aspects of the disclosed embodiment the change in a predetermined characteristic of the sample group holder is a change in orientation from a nominal orientation of the sample group holder on a pick table of the apparatus.

In accordance with one or more aspects of the disclosed embodiment the apparatus further includes a gantry system wherein the pick head is mounted to a movable member of the gantry system.

In accordance with one or more aspects of the disclosed embodiment the at least one predetermined feature is an edge of the sample group holder.

In accordance with one or more aspects of the disclosed embodiment the sample group holder comprises a tray configured for holding a group of sample containers, and the edge is an edge of the tray.

In accordance with one or more aspects of the disclosed embodiment the at least one predetermined feature is a boundary of a group of sample containers contained in the sample group holder.

In accordance with one or more aspects of the disclosed embodiment a sample storage and retrieval system is provided. The sample storage and retrieval system includes a frame, a pick table mounted to the frame and configured to hold at least one sample group holder thereon, a movable pick head mounted to the frame, the movable pick head having at least one sensor connected thereto, the sensor being configured to detect one or more features of the at least one sample group holder, and a controller operatively coupled to the movable pick head and the at least one sensor, the controller being configured to determine a dimensional change of the at least one sample group holder based on a detection signal from the at least one sensor, the detection signal corresponding to detection of the one or more features of the at least one sample group holder, and determine a location of at least one sample in the at least one sample group holder based on the dimensional change.

In accordance with one or more aspects of the disclosed embodiment the dimensional change of the at least one sample group holder is a temperature dependent dimensional change.

In accordance with one or more aspects of the disclosed embodiment the frame forms a sample picking area maintained at a picking temperature, the sample storage and retrieval system further comprising a sample storage area communicably coupled to the picking area and maintained at a storage temperature that is lower than the picking temperate.

In accordance with one or more aspects of the disclosed embodiment the controller is configured to determine the dimensional change of the at least one sample group holder at predetermined time intervals to account for dimensional changes in the at least one sample group holder as a temperature of the at least one sample group holder increases.

In accordance with one or more aspects of the disclosed embodiment the controller is configured to determine the dimensional change of the at least one sample group holder when a pick of a sample within the at least one sample group holder is missed.

In accordance with one or more aspects of the disclosed embodiment the controller is further configured to determine a position of the at least one sample group holder relative to a nominal sample group holder position on the pick table based on the detected one or more features of the at least one sample group holder.

In accordance with one or more aspects of the disclosed embodiment the controller is further configured to determine an orientation of the at least one sample group holder relative to a nominal sample group holder orientation on the pick table based on the detected one or more features of the at least one sample group holder.

In accordance with one or more aspects of the disclosed embodiment the pick head is configured to cut a seal of the sample containers within the at least one sample group holder for separating the containers.

In accordance with one or more aspects of the disclosed embodiment the one or more features of the at least one sample group holder include one or more edges of the sample group holder.

In accordance with one or more aspects of the disclosed embodiment the controller is configured to compare a measured dimension of the at least one sample group holder with a nominal dimension of the at least one sample group holder and determine at least one dimensional offset and determine a location of at least one sample in the at least one sample group holder based on the at least one dimensional offset.

In accordance with one or more aspects of the disclosed embodiment a sample storage and retrieval system is provided. The sample storage and retrieval system includes a frame, a pick table mounted to the frame and configured to hold at least one sample group holder thereon, a movable pick head mounted to the frame, the movable pick head having at least one sensor connected thereto, the sensor being configured to detect one or more features of the at least one sample group holder and produce a detection signal corresponding to the one or more features, and a controller operatively coupled to the movable pick head and the at least one sensor, the controller being configured to determine a sample group holder measurement of the at least one sample group holder based on the detection signal from the at least one sensor and determine one or more of a spacing between samples within the sample group holder and locations of the sample centers within the sample group holder.

It should be understood that the foregoing description is only illustrative of the aspects of the disclosed embodiment. Various alternatives and modifications can be devised by those skilled in the art without departing from the aspects of the disclosed embodiment. Accordingly, the aspects of the disclosed embodiment are intended to embrace all such alternatives, modifications and variances that fall within the scope of the appended claims. Further, the mere fact that different features are recited in mutually different dependent or independent claims does not indicate that a combination of these features cannot be advantageously used, such a combination remaining within the scope of the aspects of the invention.

What is claimed is:

1. An apparatus comprising:
   a pick head configured to transfer sample containers to and from a sample group holder;
   at least one sensor connected to the pick head and configured to detect at least one predetermined feature of the sample group holder; and
   a controller configured to
      receive a detection signal from the at least one sensor corresponding to detection of the at least one predetermined feature,
      determine a thermal growth or shrinkage change in a dimension of a predetermined physical characteristic intrinsic to the sample group holder based on a detected position of the at least one predetermined feature, and
      determine a location of one or more sample containers in the sample group holder to allow for the transfer of the one or more sample containers to and from the sample group holder based on the detection signal and based on the determined thermal growth or shrinkage change.

2. The apparatus of claim 1, wherein the change in the predetermined physical characteristic intrinsic to the sample group holder is a change in length from a nominal length of the sample group holder.

3. The apparatus of claim 1, wherein the change in the predetermined physical characteristic intrinsic to the sample group holder is a change in width from a nominal width of the sample group holder.

4. The apparatus of claim 1, wherein the change in the predetermined physical characteristic intrinsic to the sample group holder is a change in position from a nominal position of the sample group holder on a pick table of the apparatus.

5. The apparatus of claim 1, wherein the change in the predetermined physical characteristic intrinsic to the sample group holder is a change in orientation from a nominal orientation of the sample group holder on a pick table of the apparatus.

6. The apparatus of claim 1, further comprising a gantry system wherein the pick head is mounted to a movable member of the gantry system.

7. The apparatus of claim 1, wherein the at least one predetermined feature is an edge of the sample group holder.

8. The apparatus of claim 7, wherein the sample group holder comprises a tray configured for holding a group of sample containers, and the edge is an edge of the tray.

9. The apparatus of claim 1, wherein the at least one predetermined feature is a boundary of a group of sample containers contained in the sample group holder.

10. A sample storage and retrieval system comprising:
a frame;
a pick table mounted to the frame and configured to hold at least one sample group holder thereon;
a movable pick head mounted to the frame, the movable pick head having at least one sensor connected thereto, the sensor being configured to detect one or more features of the at least one sample group holder; and
a controller operatively coupled to the movable pick head and the at least one sensor, the controller being configured to determine a physical thermal growth or shrinkage dimensional change intrinsic to the at least one sample group holder based on a detection signal from the at least one sensor, the detection signal corresponding to detection of the one or more features of the at least one sample group holder, and determine a location of at least one sample container in the at least one sample group holder based on the physical dimensional change.

11. The sample storage and retrieval system of claim 10, wherein the physical dimensional change in the at least one sample group holder is a temperature dependent physical dimensional change.

12. The sample storage and retrieval system of claim 10, wherein the frame forms a sample picking area maintained at a picking temperature, the sample storage and retrieval system further comprising a sample storage area communicably coupled to the picking area and maintained at a storage temperature that is lower than the picking temperate.

13. The sample storage and retrieval system of claim 10, wherein the controller is configured to determine the physical dimensional change in the at least one sample group holder at predetermined time intervals to account for physical dimensional changes in the at least one sample group holder as a temperature of the at least one sample group holder increases.

14. The sample storage and retrieval system of claim 10, wherein the controller is configured to determine the physical dimensional change in the at least one sample group holder when a pick of a sample container within the at least one sample group holder is missed.

15. The sample storage and retrieval system of claim 10, wherein the controller is further configured to determine a position of the at least one sample group holder relative to a nominal sample group holder position on the pick table based on the detected one or more features of the at least one sample group holder.

16. The sample storage and retrieval system of claim 10, wherein the controller is further configured to determine an orientation of the at least one sample group holder relative to a nominal sample group holder orientation on the pick table based on the detected one or more features of the at least one sample group holder.

17. The sample storage and retrieval system of claim 10, wherein the pick head is configured to cut a seal of the sample containers within the at least one sample group holder for separating the sample containers.

18. The sample storage and retrieval system of claim 10, wherein the one or more features of the at least one sample group holder include one or more edges of the sample group holder.

19. The sample storage and retrieval system of claim 10, wherein the controller is configured to compare a measured dimension of the at least one sample group holder with a nominal dimension of the at least one sample group holder and determine at least one dimensional offset and determine a location of at least one sample in the at least one sample group holder based on the at least one dimensional offset.

20. A sample storage and retrieval system comprising:
a frame;
a pick table mounted to the frame and configured to hold at least one sample group holder thereon;
a movable pick head mounted to the frame, the movable pick head having at least one sensor connected thereto, the sensor being configured to detect one or more features of the at least one sample group holder and produce a detection signal corresponding to the one or more features; and
a controller operatively coupled to the movable pick head and the at least one sensor, the controller being configured to determine a thermal growth or shrinkage change of a sample group holder measurement intrinsic to the at least one sample group holder based on the detection signal from the at least one sensor and determine based on the sample group holder measurement and based on the determined thermal growth or shrinkage change an effect in one or more of a spacing between samples within the sample group holder and locations of the sample centers within the sample group holder.

* * * * *